United States Patent
Lee et al.

(10) Patent No.: US 12,251,687 B2
(45) Date of Patent: Mar. 18, 2025

(54) METHODS OF ETHERIFICATION

(71) Applicant: Dow Global Technologies LLC, Midland, MI (US)

(72) Inventors: Wen-Sheng Lee, Midland, MI (US); Dean Millar, Midland, MI (US); Stephen W. King, League City, TX (US)

(73) Assignee: Dow Global Technologies LLC, Midland, MI (US)

(*) Notice: Subject to any disclaimer, the term of this patent is extended or adjusted under 35 U.S.C. 154(b) by 505 days.

(21) Appl. No.: 17/641,936

(22) PCT Filed: Sep. 23, 2020

(86) PCT No.: PCT/US2020/052100
§ 371 (c)(1),
(2) Date: Mar. 10, 2022

(87) PCT Pub. No.: WO2021/067079
PCT Pub. Date: Apr. 8, 2021

(65) Prior Publication Data
US 2022/0355281 A1 Nov. 10, 2022

Related U.S. Application Data

(60) Provisional application No. 62/907,856, filed on Sep. 30, 2019.

(51) Int. Cl.
*C07C 41/06* (2006.01)
*B01J 29/70* (2006.01)
*B01J 37/16* (2006.01)
*B01J 37/28* (2006.01)

(52) U.S. Cl.
CPC ............ *B01J 29/7007* (2013.01); *B01J 37/16* (2013.01); *B01J 37/28* (2013.01); *C07C 41/06* (2013.01); *B01J 2229/186* (2013.01)

(58) Field of Classification Search
CPC ....... C07C 41/06; B01J 29/7007; B01J 37/16; B01J 37/28; B01J 2229/186
See application file for complete search history.

(56) References Cited

U.S. PATENT DOCUMENTS

| 4,219,678 A | 8/1980 | Droste et al. |
| 5,994,595 A | 11/1999 | Onda et al. |
| 7,807,615 B2 | 10/2010 | Stephan et al. |
| 2009/0240086 A1 | 9/2009 | Barsa et al. |

FOREIGN PATENT DOCUMENTS

| EP | 0419077 A2 * | 3/1991 | ............ C07C 41/06 |
| GB | 1496181 A | 12/1977 | |
| JP | 2000300994 A | 10/2000 | |
| NZ | 199281 A * | 5/1986 | ............ C07C 41/00 |
| WO | 2013146370 A1 | 10/2013 | |

OTHER PUBLICATIONS

International Search Report & Written Opinion for related PCT Application PCT/US2020/052100, mailed Dec. 17, 2020 (11 pgs).
Hu, et al., "Influence of Shaped and Modified Hb Zeolite on Etherification of FCC Light Gasoline"; Science Direct-Microporous and Mesoporous Materials, vol. 94, May 26, 2006 (5 pgs).
International Preliminary Report on Patentability for related PCT Application PCT/US2020/052100, mailed Apr. 14, 2022 (7 pgs).
Zhao et al., "Etherification of FCC Light Gasoline over P-Loaded Zeolite Beta Catalyst"; Journal of Fuel Chemistry and Technology, vol. 32, No. 2, Apr. 30, 2004, pp. 225-229.
Ruppert et al., Synthesis of long alkyl Chain Ethers through Direct etherification of biomass-based alcohols with 1-octene over heterogeneous acid catalysts; Journal of Catalysis vol. 268, Oct. 28, 2009, pp. 251-259.

* cited by examiner

*Primary Examiner* — Ana Z Muresan
(74) *Attorney, Agent, or Firm* — Arthur R. Rogers

(57) ABSTRACT

Embodiments of the present disclosure are directed towards methods of etherification including modifying a zeolite catalyst with phosphorus to provide a phosphorus modified zeolite catalyst; and contacting the phosphorus modified zeolite catalyst with an olefin and an alcohol to produce a monoalkyl ether.

7 Claims, No Drawings

METHODS OF ETHERIFICATION

This application is a National Stage Application under 35 U.S.C. § 371 of International Application Number PCT/US2020/052100, filed Sep. 23, 2020 and published as WO 2021/067079 on Apr. 8, 2021, which claims the benefit to U.S. Provisional Application 62/907,856, filed Sep. 30, 2019, the entire contents of which are incorporated herein by reference in its entirety

FIELD OF DISCLOSURE

Embodiments of the present disclosure are directed towards methods of etherification, more specifically, embodiments are directed towards methods of etherification including modifying a zeolite catalyst with phosphorus to provide a phosphorus modified zeolite catalyst and contacting the phosphorus modified zeolite catalyst with an olefin and an alcohol to produce a monoalkyl ether.

BACKGROUND

Monoalkyl ethers are useful for a number of applications such as solvents, surfactants, and chemical intermediates, for instance. There is continued focus in the industry on developing new and improved materials and/or methods that may be utilized for making monoalkyl ethers.

SUMMARY

The present disclosure provides methods of etherification, the methods including modifying a zeolite catalyst with phosphorus to provide a phosphorus modified zeolite catalyst having an atomic ratio of phosphorus to aluminum from 0.05:1 to 1.5:1 and a phosphorus loading from 0.05 to 6 weight percent based upon a total weight of the phosphorus modified zeolite catalyst; and contacting the phosphorus modified zeolite catalyst with an olefin and an alcohol to produce a monoalkyl ether.

The above summary of the present disclosure is not intended to describe each disclosed embodiment or every implementation of the present disclosure. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION

Methods of etherification are disclosed herein. The methods include modifying a zeolite catalyst with phosphorus to provide a phosphorus modified zeolite catalyst and contacting the phosphorus modified zeolite catalyst with an olefin and an alcohol to produce a monoalkyl ether.

Advantageously, the methods of etherification disclosed herein can provide an improved, i.e. greater, monoalkyl ether yield, as compared to etherifications that do not utilize the phosphorus modified zeolite catalyst, as discussed further herein. Improved monoalkyl ether yield, can be desirable for a number of applications, such as providing chemical intermediates. As an example, the monoalkyl ethers may be utilized as chemical intermediates in a surfactant production by ethoxylation process, making a greater monoalkyl ether yield desirable.

Additionally, the methods of etherification disclosed herein can provide an improved, i.e. greater, monoalkyl ether production rate, as compared to etherifications that do not utilize the phosphorus modified zeolite catalyst, as discussed further herein. Improved monoalkyl ether production rates can be desirable for a number of applications to provide desirable products with reduced production times and/or associated costs, for instance.

Zeolite catalysts are crystalline metallosilicates, e.g., aluminosilicates, constructed of repeating $TO_4$ tetrahedral units where T may be Si, Al or P (or combinations of tetrahedral units), for example. These units are linked together to form frameworks having regular intra-crystalline cavities and/or channels of molecular dimensions, e.g., micropores.

Embodiments of the present disclosure provide that the zeolite catalyst is a synthetic zeolite catalyst. Synthetic zeolite catalysts can be made by a known process of crystallization of a silica-alumina gel in the presence of alkalis and templates, for instance. Examples include zeolite beta catalysts (BEA), Linde Type A (LTA), Linde Types X and Y (Al-rich and Si-rich FAU), Silicalite-1, ZSM-5 (MFI), Linde Type B (zeolite P), Linde Type F (EDI), Linde Type L (LTL), Linde Type W (MER), and SSZ-32 (MTT) as described using IUPAC codes in accordance with nomenclature by the Structure Commission of the International Zeolite Association. IUPAC codes describing Crystal structures as delineated by the Structure Commission of the International Zeolite Association refer to the most recent designation as of the priority date of this document unless otherwise indicated.

One or more embodiments provide that the zeolite catalyst a zeolite beta (BEA) catalyst. One or more embodiments provide that the zeolite catalyst includes a number of Bronsted acid sites, i.e., sites that donate protons.

The zeolite catalyst can have a $SiO_2/Al_2O_3$ mole ratio from 5:1 to 1500:1 as measured using Neutron Activation Analysis. All individual values and subranges from 5:1 to 1500:1 are included; for example, the zeolite catalyst can have a $SiO_2/Al_2O_3$ mole ratio from a lower limit of 5:1, 10:1, 15:1, or 20:1 to an upper limit of 1500:1, 750:1, 300:1, or 100:1.

The zeolite catalyst can have a mean pore diameter from 5 to 12 angstroms. All individual values and subranges from 5 to 12 angstroms are included; for example, the zeolite catalyst can have a mean pore diameter from a lower limit of 5 or 7 angstroms to an upper limit of 11 or 12 angstroms.

The zeolite catalyst can have surface area from 130 to 1000 $m^2/g$. All individual values and subranges from 130 to 1000 $m^2/g$ are included; for example, the zeolite catalyst can have a surface area from a lower limit of 130, 150, 175, 300, 400, or 500 $m^2/g$ to an upper limit of 1000, 900, or 800 $m^2/g$. Surface area is measured according to ASTM D4365-19.

As mentioned, the zeolite catalyst can be made by a process that utilizes a template, which may also be referred to as an organic template. Templates may also be referred to as templating agents and/or structure-directing agents (SDAs). The template can be added to the reaction mixture for making the zeolite catalyst to guide, e.g., direct, the molecular shape and/or pattern of the zeolite catalyst's framework. When the zeolite catalyst making process is completed, the zeolite catalyst includes templates, e.g., templates located in the micropores of the zeolite catalyst. Templates are utilized in the formation of the zeolite catalyst. One or more embodiments provides that the template comprises ammonium ions. Zeolite catalyst that include templates can be made by known processes. Zeolite catalyst that include templates can be obtained commercially.

Examples of suitable commercially available metallosilicate catalysts include CP814E, CP814C, CP811C-300, CBV 712, CBV 720, CBV 760, CBV 2314, CBV 10A from ZEOLYST INTERNATIONAL™ of Conshohocken, PA.

Various templates that may be utilized for making zeolite catalysts are known. Examples of templates include tetraethylammonium hydroxide; N,N,N-trimethyl-1-adamanteammonium hydroxide; hexamethyleneimine; and dibenzylmethylammonium; among others.

Embodiments of the present disclosure provide modifying a zeolite catalyst with phosphorus to provide a phosphorus modified zeolite catalyst. The phosphorus modification, e.g., phosphatation, may comprise impregnation. Impregnation may be referred to as incipient wetness impregnation or wet impregnation. Modifying the zeolite catalyst with phosphorus may utilize known conditions, e.g., known phosphorous impregnation conditions, and may utilize know equipment and known components. For instance, the zeolite catalyst may be contacted with an aqueous solution including a phosphorous compound. Examples of the phosphorous compound include, but are not limited to, phosphoric acid, monoammonium phosphate, diammonium phosphate, sodium phosphate, disodium phosphate, and combinations thereof.

Modifying a zeolite catalyst with phosphorus can include contacting the zeolite catalyst with a solution including a phosphorous compound. The solution may include water. Various amounts of phosphorous compound and/or water may be utilized for different applications.

The zeolite catalyst may be contacted with the aqueous solution including the phosphorous compound at temperature from 5° C. to 90° C. All individual values and subranges from 5° C. to 90° C. are included; for example, the zeolite catalyst may be contacted with the aqueous solution including the phosphorous compound at temperature from a lower limit of 5, 10, or 15° C. to an upper limit of 90, 85, or 80° C. The zeolite catalyst may be contacted with the aqueous solution including the phosphorous compound for various times for different applications.

Embodiments of the present disclosure provide that the phosphorus modified zeolite catalyst has an atomic ratio of phosphorus to aluminum from 0.05:1 to 1.5:1. All individual values and subranges from 0.05:1 to 1.5:1 are included; for example, the phosphorus modified zeolite catalyst can have an atomic ratio of phosphorus to aluminum from a lower limit of 0.05:1, 0.075:1, 0.10:1 or to an upper limit of 1.5:1, 1.3:1, or 1.2:1. The atomic ratio of phosphorus to aluminum is determined by a known process. The atomic ratio of phosphorus to aluminum is calculated based upon components utilized to make the phosphorus modified zeolite catalyst. For instance, known amounts of phosphorus and aluminum of the zeolite catalyst, e.g., based upon a structure of the zeolite catalyst, and a known amount of phosphorus utilized to make the phosphorus modified zeolite catalyst are utilized to calculate the atomic ratio of phosphorus to aluminum of the phosphorus modified zeolite catalyst.

Embodiments of the present disclosure provide that the phosphorus modified zeolite catalyst has a phosphorus loading, e.g., phosphorous provided via the phosphorus modification discussed herein, from 0.05 to 6 weight percent based upon a total weight of the phosphorus modified zeolite catalyst. All individual values and subranges from 0.05 to 6 weight percent are included; for example, the phosphorus modified zeolite catalyst can have a phosphorus loading from a lower limit of 0.05, 1.0, or 2.0 weight percent to an upper limit of 6, 5.5, or 4.5 weight percent based upon a total weight of the phosphorus modified zeolite catalyst. Phosphorus loading may be determined by a known process. For instance, phosphorus loading, e.g., nominal phosphorus loading, may be calculated based upon components utilized to make the phosphorus modified zeolite catalyst.

One or more embodiments of the present disclosure provide that following the modification with phosphorous, the phosphorus modified zeolite catalyst can be calcined. The phosphorus modified zeolite catalyst can be calcined at a temperature from 350° C. to 700° C. All individual values and subranges from 350° C. to 700° C. are included; for example, the phosphorus modified zeolite catalyst may be calcined at from a lower limit of 350° C., 400° C., or 450° C. to an upper limit of 700° C., 650° C., or 600° C.

The phosphorus modified zeolite catalyst can be calcined in a number of known calcination environments. For instance, the phosphorus modified zeolite catalyst can be calcined in an air environment.

The phosphorus modified zeolite catalyst can be calcined, i.e., exposed to a temperature from 350° C. to 700° C. in a calcination environment, from 1 hour to 24 hours. All individual values and subranges from 1 hour to 24 hours are included; for example, the phosphorus modified zeolite catalyst may be calcined at from a lower limit of 1 hour, 3 hours, or 6 hours to an upper limit of 24 hours, 18 hours, or 12 hours.

One or more embodiments provide that the methods disclosed herein include reducing e.g., removing, templates of the zeolite catalyst prior to the phosphorus modifying as discussed herein. Embodiments of the present disclosure provide that templates of the zeolite catalyst can be reduced by calcination.

To reduce templates, the zeolite catalyst may be calcined at temperature from 525° C. to 750° C. All individual values and subranges from 525° C. to 750° C. are included; for example, the zeolite catalyst may be calcined at from a lower limit of 525° C., 550° C., or 575° C. to an upper limit of 750° C., 700° C., or 650° C. to reduce templates.

To reduce templates, the zeolite catalyst may be calcined in a number of known calcination environments. For instance, the zeolite catalyst may be calcined in an air environment.

To reduce templates, the zeolite catalyst may be calcined, i.e., exposed to a temperature from 525° C. to 750° C. in a calcination environment, from 1 hour to 24 hours. All individual values and subranges from 1 hour to 24 hours are included; for example, the zeolite catalyst may be calcined at from a lower limit of 1 hour, 3 hours, or 6 hours to an upper limit of 24 hours, 18 hours, or 12 hours.

Embodiments of the present disclosure are directed towards methods of etherification. Etherification refers to a chemical process, e.g., chemical reaction, that produces ethers. The methods disclosed herein include contacting the phosphorus modified zeolite catalyst with an olefin and an alcohol to produce a monoalkyl ether.

As used herein, "olefin" refers to a compound that is a hydrocarbon having one or more carbon-carbon double bonds. Embodiments of the present disclosure provide that the olefin includes from 6 to 30 carbon atoms. All individual values and subranges from 6 to 30 carbon atoms are included; for example, the olefin can include a lower limit of 6, 8, or 10 carbons to an upper limit of 30, 20, or 14 carbons.

The olefin may include alkenes such as alpha (α) olefins, internal disubstituted olefins, or cyclic structures (e.g., $C_3$-$C_{12}$ cycloalkene). Alpha olefins include an unsaturated bond in the α-position of the olefin. Suitable α olefins may be selected from the group consisting of propylene, 1-butene, 1-hexene, 4-methyl-1-pentene, 1-heptene, 1-octene, 1-decene, 1-dodecene, 1-tetradecene, 1-hexadecene, 1-octadecene, 1-icosene, 1-docosene and combinations thereof. Internal disubstituted olefins include an unsaturated bond not in a terminal location on the olefin. Internal olefins may be selected from the group consisting of 2-butene, 2-pentene, 2-hexene, 3-hexene, 2-heptene, 3-heptene, 2-octene, 3-octene, 4-octene, 2-nonene, 3-nonene, 4-nonene, 2-decene, 3-decene, 4-decene, 5-decene and combinations thereof. Other exemplary olefins may include butadiene and styrene.

Examples of suitable commercially available olefins include NEODENE™6-XHP, NEODENE™ 8, NEODENE™ 10, NEODENE™ 12, NEODENE™ 14, NEODENE™ 16, NEODENE™ 1214, NEODENE™1416, NEODENE™ 16148 from Shell, The Hague, Netherlands.

Embodiments of the present disclosure provide that the alcohol may comprise a single hydroxyl group, may comprise two hydroxyl groups, i.e., a glycol, or may comprise three hydroxyl groups. The alcohol may include 1 carbon or greater, or 2 carbons or greater, or 3 carbons or greater, or 4 carbons or greater, or 5 carbons or greater, or 6 carbons or greater, or 7 carbons or greater, or 8 carbons or greater, or 9 carbons or greater, while at the same time, 10 carbons or less, or 9 carbons or less, or 8 carbons or less, or 7 carbons or less, or 6 carbons or less, or 5 carbons or less, or 4 carbons or less, or 3 carbons or less, or 2 carbons or less. The alcohol may be selected from the group consisting of methanol, ethanol, monoethylene glycol, diethylene glycol, propylene glycol, triethylene glycol, polyethylene glycol, monopropylene glycol, dipropylene glycol, tripropylene glycol, polypropylene glycol, 1,3-propanediol, 1,2-butanediol, 2,3-butanediol, 1,4-butanediol, 1,6-hexanediol, 1,4-cyclohexanemethanediol, glycerol and, combinations thereof. One or more embodiments provide that the alcohol is selected from the group consisting of monoethylene glycol, diethylene glycol, glycerol, and combinations thereof. One or more embodiments provide that the alcohol is a (poly)alkylene glycol such as monoethylene glycol, diethylene glycol, propylene glycol, or triethylene glycol. Examples of (poly)alkylene glycols include monoethylene glycol, diethylene glycol, triethylene glycol, polyethylene glycol, monopropylene glycol, dipropylene glycol, tripropylene glycol, polypropylene glycol, 1,3-propane diol, 1,2-butane diol, 2,3-butane diol, 1,4-butane diol, 1,6-hexane diol, paraxylene glycol, glycerol, and 1,4-cyclohexane methane diol. One or more embodiments provide that the (poly)alkylene glycol is monoethylene glycol.

Embodiments of the present disclosure provide that the alcohol and the olefin are reacted at a molar ratio of 0.05:1 to 20:1 moles of alcohol to moles of olefin. All individual values and subranges from 0.05:1 to 20:1 are included; for example, the alcohol and the olefin can be reacted at lower limit of 0.05:1, 0.075:1, or 0.1:1 to an upper limit of 20:1, 18:1, or 15:1 moles of alcohol to moles of olefin.

As mentioned, methods disclosed herein include contacting the phosphorus modified zeolite catalyst with an olefin and an alcohol to produce a monoalkyl ether. The olefin and the alcohol may contact the phosphorus modified zeolite catalyst under known etherification conditions and may utilize know reaction equipment and known reaction components. For instance, the olefin and the alcohol may contact the phosphorus modified zeolite catalyst in a slurry reactor, a fixed-bed reactor, or a fluidized-bed reactor. The reactor may operate in batch mode or continuous mode.

The phosphorus modified zeolite catalyst may be utilized in an amount such that the phosphorus modified zeolite catalyst is from 1% to 50% by weight based upon a total weight of the olefin, for instance. All individual values and subranges from 1% to 50% by weight are included; for example, the(phosphorus modified zeolite catalyst can be from a lower limit of 1%, 3%, or 5% to an upper limit of 50%, 40%, or 30% by weight based upon a total weight of the olefin.

The olefin and the alcohol may contact the phosphorus modified zeolite catalyst at a reaction temperature from 80° C. to 200° C. All individual values and subranges from 80° C. to 200° C. are included; for example, the olefin and the alcohol may contact the phosphorus modified zeolite catalyst from a lower limit of 80, 90, or 100° C. to an upper limit of 200, 175, or 150° C.

The reaction pressure may vary for different applications. For instance, the reaction pressure may be a reduced pressure, an atmospheric pressure, or an increased pressure.

Contacting the phosphorus modified zeolite catalyst with the olefin and the alcohol produces a monoalkyl ether. Various monoalkyl ethers may be produced for different applications, e.g., by varying which olefin is utilized and/or by varying which alcohol is utilized. Advantageously, the methods of etherification disclosed herein can provide an improved, i.e. greater, monoalkyl ether yield, as compared to etherifications that do not utilize the phosphorus modified zeolite catalyst as described herein.

Additionally, the methods of etherification disclosed herein can provide an improved, i.e. greater, monoalkyl ether production rate, as compared to etherifications that do not utilize the phosphorus modified zeolite catalyst as described herein.

EXAMPLES

In the Examples, various terms and designations for materials are used including, for instance, the following:

Zeolite beta catalyst (CP 814E, CAS No. 1318-02-1, $SiO_2/Al_2O_3$ mole ratio of 25:1; mean pore diameter 6.7 angstroms; surface area 680 $m^2/g$; all organic templates were removed by commercial supplier prior to receipt; obtained from Zeolyst International);

Zeolite beta catalyst (CP 806EL, CAS No. 1318-02-1; $SiO_2/Al_2O_3$ mole ratio of 25:1; mean pore diameter angstroms; surface area 177 $m^2/g$; including organic templates as obtained; obtained from Zeolyst International).

Example 1 was performed as follows. Zeolite beta catalyst (CP 806EL) was calcined at 550° C. in an air environment for 12 hours to remove the templates from the zeolite beta catalyst. Then, the zeolite beta catalyst having the templates removed by calcination was modified with phosphorous as follows. The zeolite beta catalyst (50 grams) and an aqueous phosphoric acid solution (2.2 grams phosphoric acid; 120 grams deionized water) were added to a container with constant stirring for approximately 10 minutes at room temperature to provide a phosphorus modified zeolite catalyst. The phosphorus modified zeolite catalyst was dried in a box oven at 80° C. for 1 hour, and then calcined at 550° C. in an air environment for 8 hours. The phosphorus modified zeolite catalyst was calculated to have a nominal phosphorus content of 1.4 weight percent based upon a total weight of the phosphorus modified zeolite catalyst, and a phosphorus/aluminum atomic ratio of 0.38:1.

Etherification was performed as follows. The phosphorus modified zeolite catalyst (0.75 grams) was added to a vial reactor (40 mL) with rare earth magnetic stir bars (Part #: VP 772FN-13-13-150, V&P Scientific, Inc.); 1-dodecene (6.2 grams) and monoethylene glycol (6.7 grams) were added to the vial reactor; the contents of the vial reactor were heated to 135° C. and stirred for 3 hours for the etherification. Then the contents of the vial reactor were analyzed by gas chromatography. The gas chromatography samples were prepared by adding contents of the vial reactor (100 μL) to 10 mL of internal standard solution (1 mL of hexadecane dissolved in 1 L of ethyl acetate) and were then analyzed offline with an Agilent GC (7890). For the analysis, dioxane, 1-dodecene (1-$C_{12}$) and isomers thereof ($C_{12}$), 2-dodecanol, diethylene glycol, monoalkyl ether and isomers thereof, and dialkyl ether and isomers thereof were included for product quantification such that the weight percent of species of interests were obtained.

Monoalkyl ether production rate (grams/hour/grams zeolite beta catalyst) was determined as follows: [net change of $C_{12}$ conversion×g of 1-$C_{12}$ loaded×ME selectivity/168.32× 230.39/g of catalyst/reaction time in h].

Dodecene derived species were monoether, diether, and 2-dodecanol.

Total amount of dodecene derived species=monoether moles+2× diether moles+2-dodecanol.

Total amount of dodecene, which includes 1-dodecene and all non 1-dodecene other $C_{12}$ isomers.

Dodecyl-monoether (ME) selectivity (%) was determined as: [total amount of ME]/[total amount of $C_{12}$ derived species]×100%.

Dodecyl-diether (DE) selectivity (%) was determined as: 2×[total amount of DE]/[total amount of $C_{12}$ derived species]×100%.

Olefin conversion (%) was determined as: [total amount of $C_{12}$ derived species]/[total amount of $C_{12}$ derived species+total amount of dodecene]×100%.

Dodecyl-monoether (ME) yield (%) was determined as: $C_{12}$ conversion×dodecyl-monoether selectivity.

The results are reported in Table 1.

Example 2 was performed the same as Example 1 with the change that the aqueous phosphoric acid solution included 4.0 grams phosphoric acid and 120 grams of deionized water.

Example 3 was performed the same as Example 1 with the change that the aqueous phosphoric acid solution included 6.5 grams phosphoric acid and 120 grams of deionized water.

Comparative Example A was performed the same as Example 1 with the change that 23 grams of the zeolite beta catalyst in which the templates were removed by calcination was utilized, and the aqueous phosphoric acid solution included 6.8 grams phosphoric acid and 4.9 grams of deionized water.

Comparative Example B was performed the same as Example 1 the change that the zeolite beta catalyst was not modified with phosphorus, i.e., no aqueous phosphoric acid solution was utilized.

TABLE 1

|  | Example 1 | Example 2 | Example 3 | Comparative Example A | Comparative Example B |
|---|---|---|---|---|---|
| Nominal phosphorous loading (wt %) | 1.4 | 2.5 | 4.1 | 9.3 | — |
| P/Al atomic ratio | 0.38:1 | 0.68:1 | 1.12:1 | 2.53:1 | — |
| Monoalkyl ether yield (%) | 33.5 | 33.9 | 32.0 | 16.1 | 22.7 |
| Monoalkyl ether production rate (grams/hour/ grams zeolite beta catalyst) | 1.3 | 1.3 | 1.2 | 0.6 | 0.9 |
| Monoalkyl ether selectivity (%) | 88.1 | 88.3 | 81.9 | 84.7 | 91.9 |
| Dialkyl ether selectivity (%) | 11.4 | 11.0 | 18.1 | 15.3 | 7.1 |
| Olefin conversion (%) | 38.0 | 38.4 | 39.1 | 19.0 | 24.7 |

The data of Table 1 illustrate that each of Examples 1-3 had an improved, i.e. greater, monoalkyl ether yield as compared to each of Comparative Examples A-B.

The data of Table 1 illustrate that each of Examples 1-3 had an improved, i.e. greater, monoalkyl ether production rate as compared to each of Comparative Examples A-B.

Example 4 was performed as follows. Zeolite beta catalyst (CP 814E) was calcined at 550° C. in an air environment for 12 hours to convert the catalyst from $NH_4$ form to H form; then the catalyst was modified with phosphorous as follows. Zeolite beta catalyst (7 grams) and an aqueous phosphoric acid solution (0.3 grams phosphoric acid; 14 grams deionized water) were added to a container and stirred for approximately 10 minutes at room temperature to provide a phosphorus modified zeolite catalyst. The phosphorus modified zeolite catalyst was dried in a box oven at 80° C. for 1 hour, and then calcined at 550° C. in an air environment for 5 hours. The phosphorus modified zeolite catalyst was calculated to have a nominal phosphorus content of 1.4 weight percent based upon a total weight of the phosphorus modified zeolite catalyst, and a phosphorus/aluminum atomic ratio of 0.38:1. Etherification was performed as previously discussed with the change that the contents of the vial reactor were heated to 125° C. rather than 135° C. for the etherification and the etherification was for 3 hours; etherification results were determined as previously discussed.

Example 5 was performed as Example 4 with the change that the aqueous phosphoric acid solution included 0.58 grams phosphoric acid and 14 grams of deionized water.

Comparative Example C was performed as Example 4 with the change that 9 grams of zeolite beta catalyst (H form) was utilized, and the aqueous phosphoric acid solution included 2.35 grams phosphoric acid and 18 grams of deionized water.

Comparative Example D was performed as Example 4 with the change that the zeolite beta catalyst was not modified with phosphorus, i.e., no aqueous phosphoric acid solution was utilized.

The results are reported in Table 2.

TABLE 2

|  | Example 4 | Example 5 | Comparative Example C | Comparative Example D |
|---|---|---|---|---|
| Nominal phosphorous loading (wt %) | 1.4 | 2.6 | 8.25 | — |

TABLE 2-continued

|  | Example 4 | Example 5 | Comparative Example C | Comparative Example D |
|---|---|---|---|---|
| P/Al atomic ratio | 0.38:1 | 0.76:1 | 2.20:1 | — |
| Monoalkyl ether yield (%) | 20.9 | 24.1 | 1.8 | 12.5 |
| Monoalkyl ether production rate (grams/hour/grams zeolite beta catalyst) | 0.8 | 0.9 | 0.1 | 0.5 |
| Monoalkyl ether selectivity (%) | 81.1 | 78.0 | 96.2 | 81.4 |
| Dialkyl ether selectivity (%) | 18.3 | 21.4 | 3.8 | 18.1 |
| Olefin conversion (%) | 25.7 | 30.9 | 1.9 | 15.4 |

The data of Table 2 illustrate that each of Examples 4-5 had an improved, i.e. greater, monoalkyl ether yield as compared to each of Comparative Examples C-D.

The data of Table 2 illustrate that each of Examples 3-4 had an improved, i.e. greater, monoalkyl ether production rate as compared to each of Comparative Examples C-D.

Example 6 was performed as Example 4 with the change that 5 grams of zeolite beta catalyst (H form) was utilized, the aqueous phosphoric acid solution included 0.07 grams phosphoric acid and 10 grams of deionized water; and for the etherification, the contents of the vial reactor were heated to 150° C. rather than 135° C. and the reaction was for 1 hour.

Example 7 was performed as Example 4 with the change that 7.5 grams of zeolite beta catalyst (H form) was utilized, the aqueous phosphoric acid solution included 0.03 grams phosphoric acid and 15 grams of deionized water; and for the etherification, the contents of the vial reactor were heated to 150° C. rather than 135° C. and the reaction was for 1 hour.

Comparative Example E was performed as Example 4 with the change that 5 grams of zeolite beta catalyst (H form) was utilized, the aqueous phosphoric acid solution included 1.0 grams phosphoric acid and 10 grams of deionized water; and for the etherification, the contents of the vial reactor were heated to 150° C. rather than 135° C. and the reaction was for 1 hour.

Comparative Example F was performed as Example 4 with the change that the zeolite beta catalyst was not modified with phosphorus, i.e., no aqueous phosphoric acid solution was utilized; and for the etherification, the contents of the vial reactor were heated to 150° C. rather than 135° C. and the reaction was for 1 hour.

The results are reported in Table 3.

TABLE 3

|  | Example 6 | Example 7 | Comparative Example E | Comparative Example F |
|---|---|---|---|---|
| Nominal phosphorous loading (wt %) | 0.44 | 0.13 | 6.3 | — |
| P/Al atomic ratio | 0.11:1 | 0.04:1 | 1.7:1 | — |
| Monoalkyl ether yield (%) | 13.1 | 12.8 | 5.3 | 11.3 |
| Monoalkyl ether production rate (grams/hour/grams zeolite beta catalyst) | 5.5 | 5.4 | 2.3 | 4.8 |
| Monoalkyl ether selectivity (%) | 94 | 94 | 91 | 94 |
| Dialkyl ether selectivity (%) | 6 | 6 | 5 | 6 |
| Olefin conversion (%) | 14.0 | 13.6 | 5.8 | 12.1 |

The data of Table 3 illustrate that each of Examples 6-7 had an improved, i.e. greater, monoalkyl ether yield as compared to each of Comparative Examples E-F.

The data of Table 3 illustrate that each of Examples 6-7 had an improved, i.e. greater, monoalkyl ether production rate as compared to each of Comparative Examples E-F.

What is claimed is:

1. A method of etherification, the method comprising:
   contacting a phosphorus modified zeolite catalyst with an olefin and a (poly) alkylene glycol to produce a monoalkyl ether;
   wherein the phosphorus modified zeolite catalyst has an atomic ratio of phosphorus to aluminum from 0.05:1 to 1.5:1 and a phosphorus loading from 0.05 to 6 weight percent based upon a total weight of the phosphorus modified zeolite catalyst.

2. The method of claim 1, wherein the phosphorus modified zeolite catalyst is a phosphorus modified zeolite beta catalyst.

3. The method of claim 1, including reducing templates of the phosphorus modified zeolite catalyst prior to the modifying.

4. The method of claim 3, wherein reducing templates comprises calcining the zeolite catalyst.

5. The method of claim 1, wherein the olefin includes from 6 to 30 carbon atoms.

6. The method of claim 1, wherein the olefin is a $C_{12}$-$C_{14}$ olefin.

7. The method of claim 1, wherein the (poly)alkylene glycol is selected from the group consisting of monoethylene glycol, diethylene glycol, glycerol, and combinations thereof.

* * * * *